US011864931B2

(12) United States Patent
Ballard et al.

(10) Patent No.: US 11,864,931 B2
(45) Date of Patent: Jan. 9, 2024

(54) MEDICAL ORGANIZATION APPARATUS

(71) Applicants: Michael Ryan Ballard, Denver, CO (US); Aaron Treat, Denver, CO (US); Maxavier Guss, Centennial, CO (US)

(72) Inventors: Michael Ryan Ballard, Denver, CO (US); Aaron Treat, Denver, CO (US); Maxavier Guss, Centennial, CO (US)

( * ) Notice: Subject to any disclaimer, the term of this patent is extended or adjusted under 35 U.S.C. 154(b) by 839 days.

(21) Appl. No.: 16/936,623

(22) Filed: Jul. 23, 2020

(65) Prior Publication Data
US 2022/0022991 A1 Jan. 27, 2022

(51) Int. Cl.
*A61B 50/20* (2016.01)
*A61B 50/24* (2016.01)
*A61B 46/23* (2016.01)

(52) U.S. Cl.
CPC .............. *A61B 50/20* (2016.02); *A61B 46/23* (2016.02); *A61B 50/24* (2016.02)

(58) Field of Classification Search
CPC ......... A61B 50/24; A61B 46/00; A61B 50/00; A61B 46/23; A61B 50/20; A61M 25/02
USPC ......... 206/363, 571, 210, 557, 364; 604/198
See application file for complete search history.

(56) References Cited

U.S. PATENT DOCUMENTS

| 5,843,387 | A  | * | 12/1998 | Dane ........................ | A61L 2/26 206/483 |
| 6,436,357 | B1 | * | 8/2002 | Frieze ...................... | A61L 2/26 422/292 |
| 9,833,529 | B2 | * | 12/2017 | Tipton .................... | A61B 50/30 |
| 2001/0049504 | A1 | * | 12/2001 | Gautsche .............. | A61M 25/02 604/179 |
| 2004/0118410 | A1 | * | 6/2004 | Griesbach, III ....... | A61B 46/23 128/852 |
| 2013/0200023 | A1 | * | 8/2013 | Brotzman .............. | A47B 13/16 211/126.14 |
| 2017/0156811 | A1 | * | 6/2017 | Cerda ..................... | B65B 55/04 |
| 2018/0028703 | A1 | * | 2/2018 | McLaughlin .......... | A61B 50/34 |
| 2018/0311474 | A1 | * | 11/2018 | Tyler, II ................ | A61F 2/2427 |

FOREIGN PATENT DOCUMENTS

WO WO-2020078746 A1 * 4/2020 ............. A61B 50/20

\* cited by examiner

*Primary Examiner* — Rafael A Ortiz

(57) ABSTRACT

Techniques and apparatuses are provided for stabilizing, organizing, and supporting medical components for various medical procedures (e.g., such as surgical accessories such as medical drapery, medical instruments, cords, surgical tubes, etc.). An apparatus may include a platform and a channel component comprising a plurality of channels and channel locks. According to some embodiments, a sterile channel component may secure medical drapery between the channel component and the platform. Sterilized tools, cords, tubes, and other medical equipment may then be secured by the channel component providing an organized, secured, and sterilized surgical environment.

17 Claims, 12 Drawing Sheets

MEDICAL ORGANIZATION APPARATUS

BACKGROUND

The following relates generally to medical procedures, and more specifically to securing medical components.

Medical procedures such as medical exams, surgical procedures, etc. may be performed using various types of specialized equipment. For instance, for performing various medical procedures, medical offices or operating rooms may include medical instruments or medical equipment such as scalpels, forceps, needles/syringes, spreaders, clamps, saws, rods, screws, stents, catheters, Intravenous (IV) tubes, feeding tubes, inhalational anesthetic tubes, sterilized lubricants, instrument sterilization trays, and topical cleaning solutions, among many other examples.

In addition to various types of specialized equipment, medical professionals may utilize patient beds or patient tables, medical equipment tables, machine racks, medical drapery, etc. in order to facilitate both efficient and sterile medical procedures. For example, in some cases, a surgical table may be located proximate to a patient area (e.g., an area or region of a patient being operated on, such as the brain, spine, heart, etc.) in order to facilitate quick access to necessary medical equipment during a medical procedure. Further, some medical procedures may be performed such that work surfaces of the surgical table, as well as the medical instruments to be used for the medical procedure, are sterilized prior to use (e.g., and kept sterile until used for the medical procedure).

However, due to the extensive amount medical equipment that may be involved in a given medical procedure, medical professional may face challenges in managing the medical equipment during the procedure while maintaining an appropriately sterile environment. Improved techniques and devices for managing medical equipment may thus be desired.

SUMMARY

An apparatus, system, and method for securing medical components are described. Embodiments of the apparatus, system, and method include a platform with a flat surface and a channel component comprising one or more channels, wherein each of the channels is configured to admit and secure a cord during a medical procedure, and wherein the channel component is configured to attach to the platform and secure a medical drapery therebetween.

An apparatus, system, and method for securing medical components are described. Embodiments of the apparatus, system, and method include a platform with a flat surface configured to support a medical drapery and a channel component comprising a plurality of channels, wherein the channel component is substantially the same size as the platform in a first direction and is configured to attach to the platform to secure the medical drapery during a medical procedure, and wherein the plurality of channels is arranged in the first direction and is configured to admit and secure at least one cord during the medical procedure.

DETAILED DESCRIPTION

Figure 1:
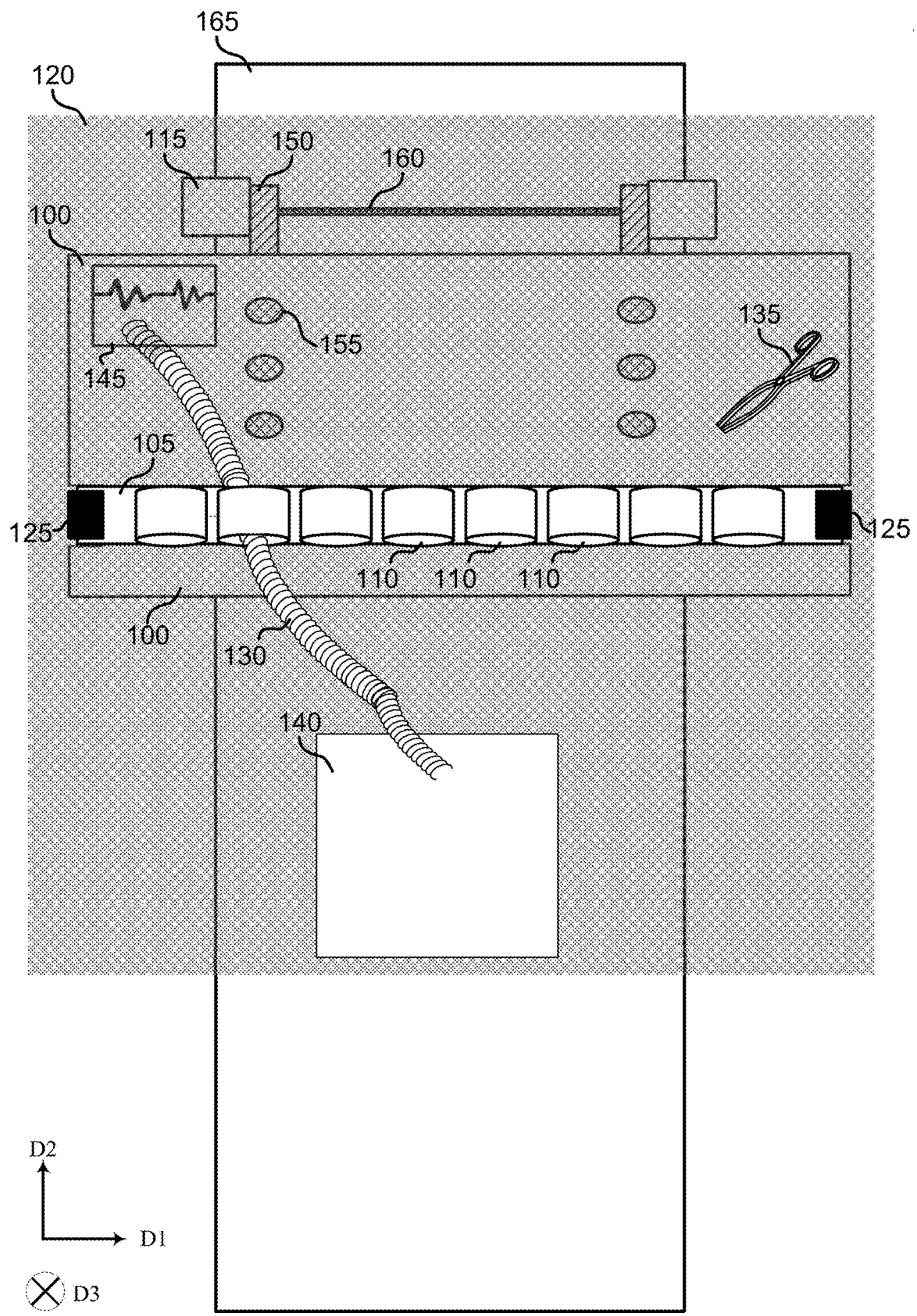
FIG. 1 shows a planer view of an example of system for securing medical components according to aspects of the present disclosure.

The present disclosure relates to medical procedures. More specifically, the present disclosure may provide techniques and apparatuses that may be used to stabilize, organize, and support surgical accessories for various surgical procedures.

Medical procedures may demand routine sterilization of a surgical environment (e.g., of medical instruments, medical tables, and various other medical equipment). In some cases (e.g., because surgical platforms and other medical tables may be large and difficult to sterilize), sterilization demands may be met via utilization of medical drapery. Medical drapery (e.g., sterilized disposable drapes, sterilized covers, surgical drapes, etc.) may refer to a barrier material used during surgical procedures to prevent contact between surfaces of tools, tables, or a surgical subject. Medical drapery may be made from single or multi-use materials. For example, such medical drapery may be laid over a surgical platform prior to the start of a medical procedure and then disposed (or later sterilized) after the procedure is complete. During a surgical procedure, transmission of pathogens or foreign material may thus be prevented with the use of medical drapery, which may lead to a reduction in the spreading of disease and infection. Further, medical instruments and other various other medical equipment may also be sterilized, for example, using dry heat, chemical vapor, steam under pressure, cold sterilization, radiation, or other sterilization techniques. For instance, a hospital or other healthcare facility may include an autoclave for sterilizing smaller medical instruments, equipment, supplies, etc.

In some cases, medical procedures may thus be associated with a large amount of equipment and important sterilization demands. For instance, a surgical procedure may be associated with extensive medical drapery in addition to various medical instruments, medical equipment, cords, etc. For example, cords (e.g., which may refer to medical equipment tubes, electrical cords, etc.) may be a component of various devices that may be used during a medical procedure to send an electrical signal, transmit power, or provide irrigation to a patient. Intravenous (IV) drips, inhalational anesthetic tubes, pulse sensors, miniature saws, water pumping devices, and various other medical equipment may be used at with a cord (e.g., or tube) during medical procedures. Accordingly, for some medical procedures, numerous cords or tubes may be attached to devices and set in place on a patient or used as medical instruments by medical professionals.

With such a large amount of medical equipment and supplies, a surgical table may become disorganized (e.g., which may result in possible misuse of the medical equipment, possible desterilization of medical equipment, inefficient or extended medical procedures, etc.). For instance, throughout some medical procedures, cords or tubes may become entangled or disorganized, may dislodge or disrupt medical drapery, may result in disorganization of other medical instruments, may provide sterilization challenges, etc. Some medical procedures may involve numerous medical components (e.g., cords, tubes, instruments, tools, etc.) surrounding a surgical table. Disorganized cords, tubes, etc. may increase patient risk of infection and result in susceptibility to cord or tube damage.

Techniques and apparatuses described herein may provide for improved organization and securement of medical components (e.g., such as medical drapery, cords and tubes, medical instruments, etc.). Further, the techniques and apparatuses described herein may provide for efficient sterilization of various medical components used to prepare for, and perform, medical procedures.

Some embodiments of the present disclosure may include a two-part apparatus design with a platform component and a channel component. The apparatus may be implemented to stabilize medical drapery, manage various cords and tubes, maintain sterilization of medical instruments and a surgical environment, stabilize a patient (e.g., with a single device), etc. The platform component may attach to a bed frame above a patient after the patient is in place for a medical procedure. Medical drapery may be placed on or around the platform for sterilization purposes. The channel component may then be attached to, or placed on, the platform component to secure the medical drapery (e.g., medical drapery may be placed between the platform and the channel component to hold the medical drapery in place for reduced pathogen or infection risk). The channel component may include channels (e.g., a sequence or row of channels) such that cords and tubes may be inserted through the channels. In some examples, the channels may be closed or locked in place to prevent cords or tubes from becoming dislodged. As such, cords and tubes may flow to the patient in an organized fashion. Various other medical components (e.g., medical instruments, sterilization trays, etc.) may also be placed and organized on the platform. For instance, organizational trays or sections may be used to organize medical instruments (e.g., surgical tools). In some cases, the platform may be adjustable for a variety of heights and locations based on the surgical procedure, surgical team, or space limitations of a room, and the channel component may secure medical drapery to the platform and maintain organization of medical components during such adjustments to the platform.

FIG. 1 shows an example of system for securing medical components according to aspects of the present disclosure. The example shown includes platform 100, channel component 105, channels 110, frame 115, medical drapery 120, attachment pieces 125, cord 130, tools 135, patient area 140, a medical machine 145, support arms 150, attachment holes 155, support rod 160, and medical table 165.

According to some embodiments, platform 100 may refer to a platform (e.g., a medical table, a surgical table, a surgical tray, etc.) with a flat surface. In some examples, the platform 100 includes one or more notches (e.g., notches 420, notches 515), and the channel component 105 may be attached to the platform 100 via attachment pieces 125 aligned with the notches with the medical drapery 120 therebetween. In some examples, the platform 100 includes one or more peg holes, and the channel component 105 includes one or more pegs (e.g., pegs 810) corresponding to the one or more peg holes, where the peg holes are configured to receive the pegs with the medical drapery 120 therebetween.

According to some embodiments, platform 100 may refer to a platform (e.g., a medical table, a surgical table, a surgical tray, etc.) with a flat surface configured to support a medical drapery 120. In some examples, the platform 100 is configured to be movable in a third direction (D3) while the attached channel component 105 secures the at least one cord 130 during the medical procedure, the third direction (D3) being substantially perpendicular to a plane formed by the first direction (D1) and the second direction (D2). In some examples, the platform 100 is configured to support one or more surgical tools 135 in addition to the attached channel component 105.

Platform 100 is an example of, or includes aspects of, the corresponding element described with reference to FIGS. 2-6, and 9.

According to some embodiments, channel component 105 comprises one or more channels 110, wherein each of the channels 110 is configured to admit and secure one or more cords 130 during a medical procedure. As described herein, the channel component 105 may be configured to attach to the platform 100 and secure a medical drapery 120 therebetween (e.g., via attachment pieces 125 and notches in the platform 100 and channel component 105, via peg holes in the platform and pegs of the channel component 105, or via various other mechanisms for attaching the channel component 105 to the platform 100). In some examples, each of the channels 110 includes a portion of a cylinder with an opening configured to receive the one or more cords 130.

In some examples, a cord 130 may include an electrical cord, a bipolar cord, a suction tube, a water tube, a drill cord, a smoke evacuation cord, an electrocautery cord, an electrical stimulation cord, various other cords, or any combination thereof. In some examples, a cord 130 may include an IV drip, feeding tubes, inhalational anesthetic tubes, various other tubes, or any combination thereof. Accordingly, as used herein, the terms "cord" and "tube" may generally be used interchangeably to refer to any components (e.g., medical components) securable by a channel component 105. A cord 130 is an example of, or includes aspects of, the corresponding elements described with reference to FIGS. 2, 3, and 7.

According to some embodiments, channel component 105 comprises a plurality of channels 110, wherein the channel component 105 is substantially the same size as the platform 100 in a first direction (D1) and is configured to attach to the platform 100 to secure the medical drapery 120 during a medical procedure. In some examples, the plurality of channels 110 is arranged in the first direction (D1) and is configured to admit and secure at least one cord 130 during the medical procedure. In some examples, each of the channels 110 in the set of channels 110 includes a portion of a cylinder with an opening configured to receive one or more cords 130, the one or more cords 130 extending from the channel component 105 along a second direction (D2) substantially perpendicular to the first direction. In some examples, the channel component 105, the channels 110, and any channel locks (e.g., channel locks 215, channel locks 315, channel lock 1000) are sterilizable.

Channel component 105 may include one or more channels 110, and various channels 110 or combinations of channels 110 may further include a channel lock as described in more detail herein. Channel component 105 is an example of, or includes aspects of, the corresponding element described with reference to FIGS. 2, 3, 8, and 9. Channels 110 are examples of, or include aspects of, the corresponding element(s) described with reference to FIGS. 2, 3, 8, and 9. Frame 115 is an example of, or includes aspects of, the corresponding element described with reference to FIGS. 2, and 4-6. Medical drapery 120 may include or refer to sterilized disposable drapes, sterilized covers, surgical drapes, or any barrier material used during surgical procedures to prevent contact or contamination between surfaces of components, tables, or a patient. Medical drapery 120 is an example of, or includes aspects of, the corresponding element described with reference to FIGS. 2, 3, 6, and 7.

According to some embodiments, attachment pieces 125 may include a top extension and a bottom extension and may be configured to secure one or more ends of the channel component 105 to one or more sides of the platform 100. In some examples, each of the one or more sides of the platform 100 comprises a groove (e.g., a notch) configured to receive the one or more attachment pieces 125, and the channel component 105 comprises an attachment notch configured to receive the top extension (e.g., as described in more detail herein, for example, with reference to FIG. 9). In some examples, the bottom extension includes an extension peg, and the platform 100 includes an extension peg hole configured to receive the extension peg.

Attachment pieces 125 may generally include or refer to any attachment devices, clamps, hinged clamps, grips, brackets, fasteners, vices, etc. Attachment pieces 125 are examples of, or include aspects of, the corresponding element(s) described with reference to FIGS. 2 and 9. Tools 135 may generally include or refer to medical components such as scalpels, forceps, needles/syringes, spreaders, clamps, saws, rods, screws, or any other medical equipment. Tool 135 is an example of, or includes aspects of, the corresponding element described with reference to FIG. 3.

In some cases, patient area 140 may refer to an area or region of a patient undergoing a medical procedure (e.g., such as a surgery). In some cases, patient area 140 may refer to an are set up by medical professionals as an area in which a surgical procedure may be performed. For instance, in some cases a patient area 140 may be formed such that a sterile environment surrounds the patient area 140 (e.g., where medical drapery 120 may surround the patient area 140, nearby medical components may be sterilized above medical drapery 120, medical components used for the medical procedure may be sterilized, etc.). Patient area 140 is an example of, or includes aspects of, the corresponding element described with reference to FIGS. 2, 3, 6, and 7. Medical machines 145 may include or refer to any medical device or machine used for medical procedures. For instance, examples of a medical machine 145 may include an IV drip bag, a feeding machine, a pulse monitor, an anesthesia machine, etc. Medical machine 145 is an example of, or includes aspects of, the corresponding element described with reference to FIG. 2.

According to some embodiments, support arms 150 are configured to attach the platform 100 to a frame 115 (e.g., a surgical bed frame). In some examples, the one or more support arms 150 may be permanently attached to the platform 100, and the channel component 105 may be separable from the platform 100. Support arms 150 are examples of, or include aspects of, the corresponding element(s) described with reference to FIGS. 2, 4, and 5. Attachment holes 155 are examples of, or include aspects of, the corresponding element(s) described with reference to FIG. 4.

According to some embodiments, support rods 160 may be configured to be inserted through first holes in the frame 115 (e.g., a surgical bed frame) and through second holes in the one or more support arms 150, thereby securing the apparatus to the frame 115. Support rods 160 are examples of, or include aspects of, the corresponding element(s) described with reference to FIGS. 2, 4, and 5. In some examples, a patient undergoing a medical procedure (e.g., surgery) may be positioned on a medical table 165. In some cases, medical table 165 may include or refer to a surgical bed. Medical table 165 is an example of, or includes aspects of, the corresponding element described with reference to FIG. 2. In some cases, frame 115 and medical table 165 may be a single component (e.g., a surgical bed frame, which may support a patient via a flat surface spanning a first and second direction, D1 and D2, and supply a mounting frame 115 in a third direction, D3)).

As further described herein (e.g., with reference to FIGS. 2 and 3), channel component 105 may be attached to the platform 100 in order to efficiently secure medical drapery 120 and facilitate sterilization of appropriate medical components (e.g., in addition to providing for improved organization of medical equipment, such as any of various cords 130 and tools 135 that may be used in a medical procedure). For instance, elements under medical drapery 120 (e.g., platform 100, various parts of frame 115 such as support arms 150, support rods 160, etc.). Alternatively, elements above medical drapery 120 (e.g., and in proximity of patient area 140) may be sterile or sterilized prior to, or during, a medical procedure. For instance, one or more medical machines 145 may be under medical drapery 120 (e.g., on platform 100 in a direction D2 away from the patient area, on the floor, etc.) and portions of one or more cords 130 attached to each of the medical machines 145 may be passed around the medical drapery 120 and through a channel 110 of the channel component 105. Accordingly, cords 130 may be sterilized and medical drapery 120 may be sterilized or disposed of after medical procedures without requiring the platform 100, the various medical machines 145, etc. be sterilized (e.g., as the medical drapery 120 may provide a barrier between non-sterilized elements or medical components and the patient area 140).

According to some embodiments, channel component 105 may include channels 110 (e.g., each channel 110 including a portion of cylinder with an opening configured to potentially receive a cord 130) and channel locks (e.g., each channel lock configured to attach to one of the channels 110, thereby confining any cords 130 to the corresponding channel 110) which may all be readily sterilized. That is, channel component 105 (e.g., and all of channel component 105 elements or subcomponents) may be separable from platform 100 and may be sterilized between medical procedures (e.g., along with other medical components such as tools 135. Accordingly, the techniques and apparatuses described herein may provide for efficient securement of medical drapery 120, improved organization of cords 130 and other tools 135, and may facilitate medical procedures (e.g., medical professionals, surgical environments, etc.) satisfying sterilization demands.

In some cases, channel component 105 (e.g., and any elements, subcomponents, or pieces of a channel component 105) may be disposable, may be sterilized with other medical instruments (e.g., with any tools 135 used in a procedure), may be sterilized and pre-packaged or included in kits of surgical instruments, may be sterilized via sterilization trays or other sterilization receptacles, etc. Accordingly, channel component 105 may be suitable for securing medical drapery 120 and organizing medical components (e.g., such as cords 130).

Further, according to some embodiments, a sterile channel component 105 may provide for secure attachment to platform 100 (e.g., and thus to a rigid or sturdy frame 115 and/or medical table 165). As such, sterile channel component 105 may be utilized to stabilize a patient or one or more aspects of patient area 140 (e.g., in addition to one or more cords 130 or any other medical components). For instance, sterile channel component 105 may be suitable for stabilizing a patient's spine for surgical procedures, in addition to stabilizing one or more tubes or cords 130 for performing the surgical procedures.

Figure 2:
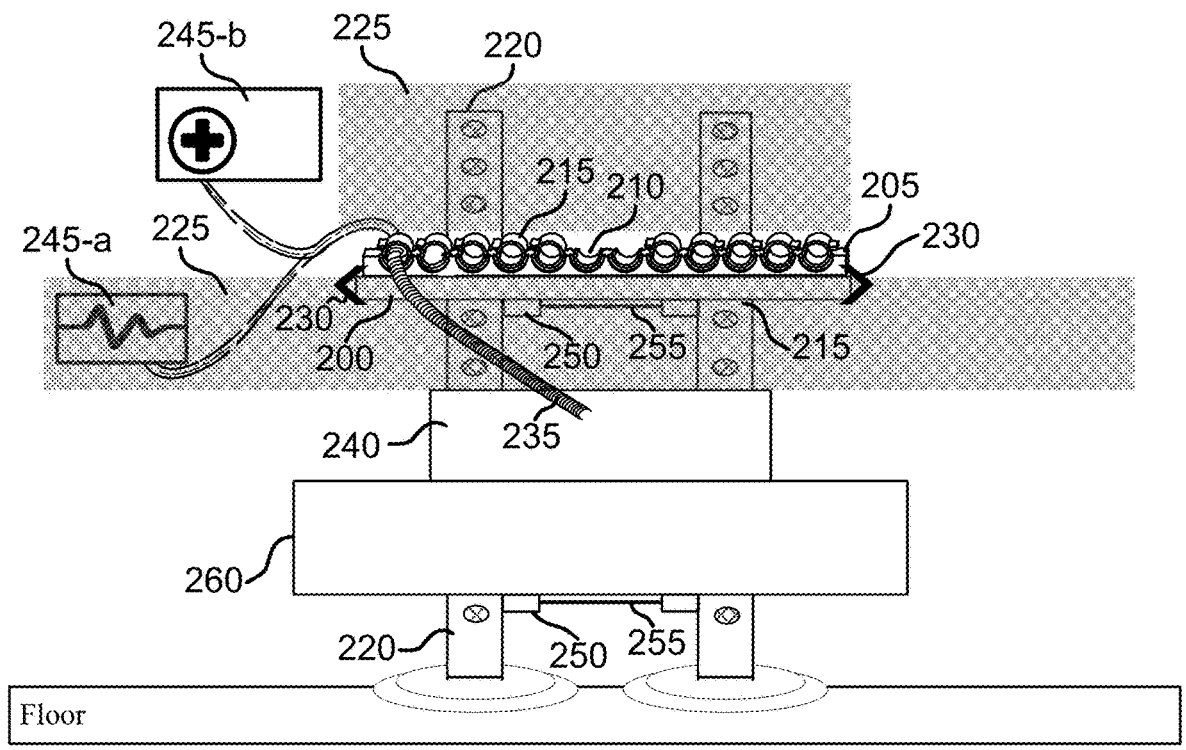
FIG. 2 shows a side view of an example of system for securing medical components according to aspects of the present disclosure.
Figure 2:
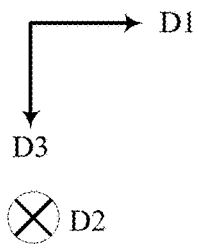

FIG. 2 shows an example of a system for securing medical components according to aspects of the present disclosure. The example shown includes platform 200, channel component 205, channels 210, channel locks 215, frame 220, medical drapery 225, attachment pieces 230, cords 235, patient area 240, medical machines 245, support arms 250, support rods 255, and medical table 260.

In some examples, a patient may be positioned on a medical table 260. A patient area 240 may then be formed or established for performing a medical procedure (e.g., such as a surgical procedure) on the patient. For example, after the patient is positioned on the medical table 260, a platform 200 may be attached near the patient area 240 and medical drapery 225 may be placed over the platform 200. In some cases, the platform 200 may be attached to support arms 250 that may secure the platform 200 to a frame 220 (e.g., via two support rods 200) going through holes in the support arms 250 and the frame 220. Channel component 205 may then be attached to platform 200 to secure medical drapery 225 therebetween (e.g., between the platform 200 and the channel component 205). For instance, channel component 205 may be attached to platform 200 via attachment pieces 230 (e.g., as further illustrated, for example, with reference to FIG. 9).

As described herein, channel component 205 may include a plurality of channels 210 (e.g., such as parallel channels 210 that may be arranged in sequence along a first direction, D1). Further, channel component 205 may include channel locks 215 corresponding to any number of the plurality of channels 210 (e.g., channel component 205 may include zero channel locks 215, channel locks 215 for each channel 210 of a subset of the plurality of channels 210, or channel locks 215 for each channel 210 of all channels of the plurality of channels 210). As described, the channels 210 each include a portion of a cylinder with an opening configured to receive one or more cords 235 and the channel locks 215 each include a sliding portion. Further, each of the channels 210 include a groove configured to receive the sliding portion, and each of the channel locks 215 further include a notch configured to secure the channel lock 215 in a closed position. Accordingly, one or more cords 235 may be secured by each channel 210 and corresponding channel lock 215 without pinching, impeding, or damaging any of the secured cords 235. As an example, for some medical procedure applications, each channel 210 and corresponding channel lock 215 combination (e.g., when closed, when locked, when in a cord 235 securing position, etc.) may have a diameter of 0.75 inches.

According to some embodiments, channel locks 215 may be configured to attach to one of the channels 210, thereby confining the cord 235 to the corresponding channel. In some examples, each of the channel locks 215 includes a sliding portion, and each of the channels 210 includes a groove configured to receive the sliding portion, and where each of the channel locks 215 further includes a notch configured to secure the channel lock in a closed position. According to some embodiments, channel locks 215 may be configured to attach to at least one channel of the plurality of channels 210, thereby confining one or more cords 235 to the corresponding channel.

Platform 200 is an example of, or includes aspects of, the corresponding element described with reference to FIGS. 1, 3-6, and 9. Channel component 205 is an example of, or includes aspects of, the corresponding element described with reference to FIGS. 1, 3, 8, and 9. Channels 210 are examples of, or include aspects of, the corresponding element(s) described with reference to FIGS. 1, 3, 8, and 9. Channel locks 215 are examples of, or include aspects of, the corresponding element(s) described with reference to FIGS. 3 and 10.

Frame 220 is an example of, or includes aspects of, the corresponding element described with reference to FIGS. 1, and 4-6. Medical drapery 225 is an example of, or includes aspects of, the corresponding element described with reference to FIGS. 1, 3, 6, and 7. Attachment pieces 230 are examples of, or include aspects of, the corresponding element(s) described with reference to FIGS. 1 and 9. Cords 235 are examples of, or include aspects of, the corresponding element(s) described with reference to FIGS. 1, 3, and 7. Patient area 240 is an example of, or includes aspects of, the corresponding element described with reference to FIGS. 1, 3, 6, and 7. Medical machines 245 are examples of, or include aspects of, the corresponding element(s) described with reference to FIG. 1.

Support arms 250 are examples of, or include aspects of, the corresponding element(s) described with reference to FIGS. 1, 4, and 5. Support rods 255 are examples of, or include aspects of, the corresponding element(s) described with reference to FIGS. 1, 4, and 5. Medical table 260 is an example of, or includes aspects of, the corresponding element described with reference to FIG. 1. In some example, frame 200 and medical table 260 may be a single component (e.g., such as a surgical bed frame 220). In other examples, frame 200 may be a separate component from medical table 260, and the frame 220 may attach to the medical table 260 via support arms 250 attached to the medical table 260 (e.g., where one or more support rods 255 may attach the medical table 260 and the frame 220 through holes in each of the medical table 260 and the frame 220).

Various platforms 200 for securing medical components may be implemented in accordance with the described techniques without departing from the scope of the present disclosure. For instance, a platform 200 may be designed and implemented based on various factors such as the surgical environment (e.g., the size of the operating room), the medical table 260 and/or the frame 220 (e.g., the type or dimensions of the medical table 260 and/or the frame 220), the medical components being used (e.g., the types of medical instruments or the amount of medical instruments), etc. As an example, a platform 200 include a platform of 12 inches in a second direction D2 (e.g., in length) and 18 inches in a first direction D1 (e.g., in width), with various heights (e.g., with various dimensions in a third direction D3). As another example, a platform 200 include a platform of 24 inches in a second direction D2 (e.g., in length) and 18 inches in a first direction D1 (e.g., in width), with various heights (e.g., with various dimensions in a third direction D3). In some cases, the platform 200 may attach directly to (e.g., and have dimensions facilitating direct attachment to) the frame 220 used in the surgical setting (e.g., such as a Jackson frame).

In some cases, platform 200 may attach to frame 220 (e.g., which in some cases may refer to a metal piece with all the holes in it, such as an "H" bracket). For instance, frame 220 (e.g., a H bracket) may have 1 hole to accept a small post in the vertical direction, and a second hole to slide the metal cylinder pin through. Brackets of other platforms 200 (e.g., platforms 200 of varying dimensions) may be designed to fit on the bed (e.g., medical table 260) the same way the H bracket is designed to fit on, accept the brackets may travel horizontally instead or vertically. In some cases, the platform may use a single pin to attach to the bed.

Figure 3:
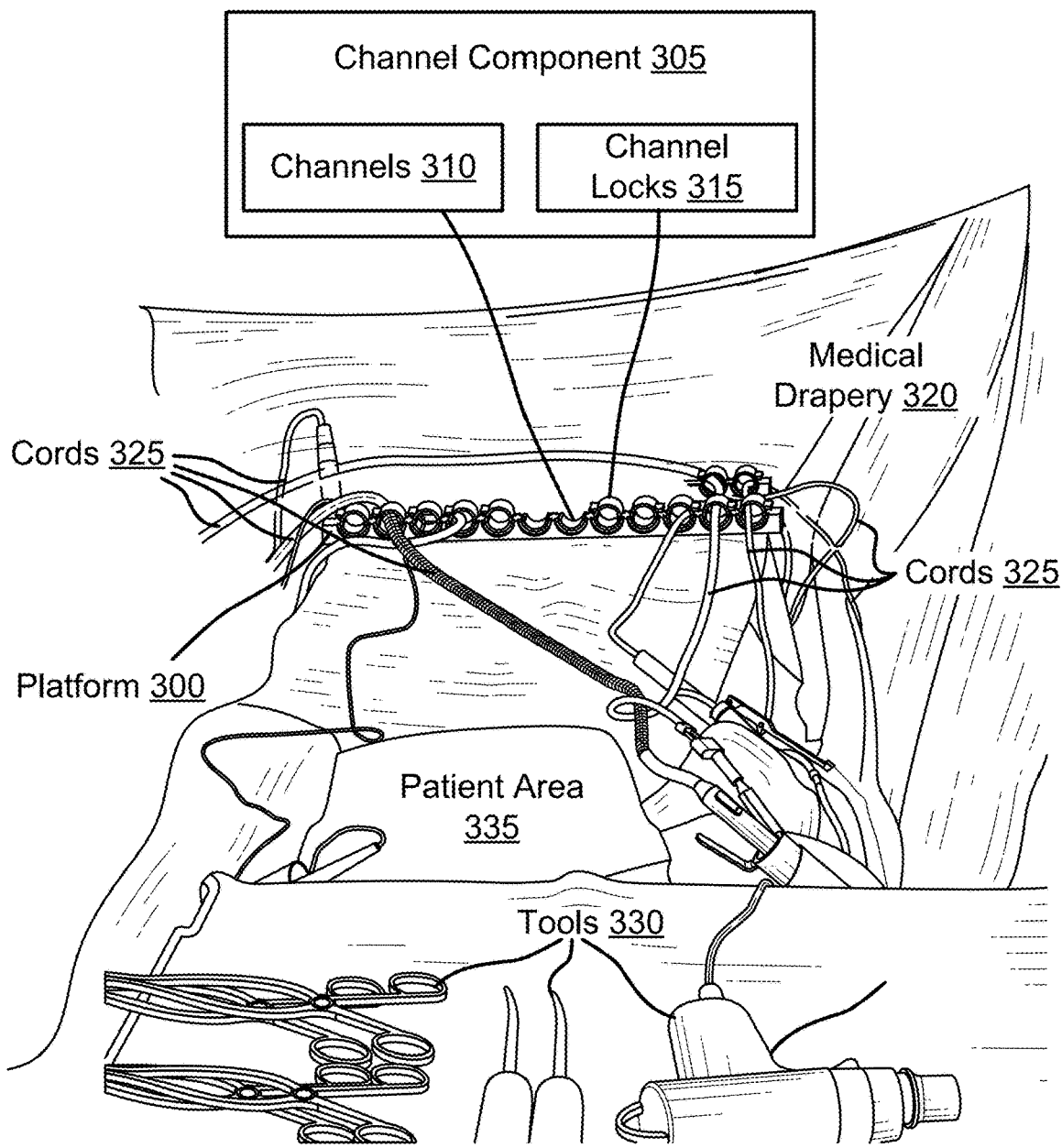
FIG. 3 shows an example of system for securing medical components according to aspects of the present disclosure.

FIG. 3 shows an example of system for securing medical components according to aspects of the present disclosure. The example shown includes platform 300, channel component 305, medical drapery 320, cords 325, tools 330, and patient area 335. FIG. 3 illustrates an example of a medical setting (e.g., a surgical operating room) where a patient area 335 may be established. For instance, as described herein, a platform 300 may be positioned over a patient prior to a medical procedure. Sterile medical drapery 320 may be placed over the platform (e.g., and in some case placed near or around patient area 335). Any medical equipment, machines, tools 330, cords 325, etc. above the medical drapery 320 may also be sterilized. Accordingly, a sterile environment may be provided around patient area 335.

Channel component 305 includes channels 310 and channel locks 315. Channel component 305 may be attached to platform 300 to secure medical drapery 320, organize various cords 325 and tools 330, support surgical accessories used in various surgical procedures, etc. In some cases, channel component 305 may be used to stabilize medical drapery 320, manage any tubing and cords 325, and stabilize a patient (e.g., stabilize the spine of a patient) all with the same device (e.g., with the channel component 305). In some cases, channel component 305 may be implemented along with robotics for certain medical procedures. For instance, channel component 305 may be implemented to organize and secure various cords 325 as well as to stabilize a patient for improved accuracy during a surgical procedure (e.g., during a surgical procedure involving robotics, where precision and accuracy may be paramount). In some examples, channel component 305 may stabilize the proximal spine/cervical spine during a medical procedure (e.g., in addition to securing medical drapery 320 for the procedure, organizing cords 325 for the procedure, etc.). In some cases, channel component 305 may stabilize a patient (e.g., the proximal spine/cervical spine) via a specialized cord 325 or a specialized frame that may be securely attached through channel component 305 (e.g., though one or more channel 310 and channel lock 315 combinations).

In some examples, a spine stabilization tool may clamp on the posterior elements of the spine (spinous processes), or attach to an existing clamp made by the implant company that attaches to the spine, and travel up to the channel component 305 (e.g., the rotolock) where it may be locked in place with a locking mechanism that stabilizes the device in space. In some cases, this device may have two arms (e.g., two "snakelike" arms, two gooseneck tubes, etc.) that may come from the edges of the channel component 305 (e.g., the rotolock) down to the center-point of the incision (spine within patient area 335) and attach to a designed spine clamp. Such may triangulate the spine and 2 edges of the channel component 305 (e.g., the rotolock) to create stability.

Generally, various sterilized devices may attach to platform 300. For instance, sterilized devices that may attach to platform 300 (e.g., via channel component 305 or via additional components) may include a device to hold a tray of implants, a device that may hold different tools that a robot may grab or utilize (e.g., at different times of a surgery), etc. For example, some surgical robots may include an arm performing certain surgical functions and the platform 300, channel component 305, etc. may support an additional robot arm that may be implemented during a medical procedure for grabbing various tools, implants, etc. In some cases, a spine implant rack may be attached to platform 300. In some cases, tools 330 (e.g., tools that cut bone, such as a bone scalpel) to be used by a robot may be secured and organized by platform 300 (e.g., and/or channel component 305) to hold the tools 330 in place (e.g., while not in use by a medical professional or by a robot). In some examples, a tool caddy may hold tools 330 vertically and the robot may be configured to identify or organize where those tools 330 are (e.g., such that the robot may access the tools 330 for usage, for instance, similar to a computer numerical control (CNC) machine that may automatically change a bit depending on what cuts are needed).

According to some embodiments, an apparatus described herein may include a two-piece design including a roto-lock platform (e.g., a platform 300) and a roto-lock stabilization system (e.g., a channel component 305). Platform 300 may include a non-sterile (e.g., but clean) flat surface such as a tray, table, bed accessory, etc. Platform 300 may attach to a frame (e.g., a frame as described with reference to FIGS. 1, 2, and 4-6). For example, platform 300 may attach to bed frames used in orthopedics (e.g., such as a Jackson table). As described, platform 300 may be attached to a frame after the patient has been positioned (e.g., after the patient has been positioned on a bed frame, on a medical table, etc.). Platform 300 may be used as a foundation for attaching a sterile channel component 305 system, and platform 300 may further be used as a storage shelf for various tools 330, as a stabilization platform (e.g., for stabilization of a spine), etc. As illustrated in more detail, for example, with reference to FIGS. 4 and 5, platform 300 may include two milled brackets (e.g., frame brackets or frame components) and one milled platform (e.g., one plastic milled platform). Accordingly, a ben may be able to move higher or lower (e.g., in a third direction, D3, with reference to FIGS. 1 and 2) to allow imaging to enter the surgical field without disassembling cords and moving surgical tools. That is, the channel component 305 and the platform 300 apparatus described herein may provide for increased mobility of either the patient and/or the channel component 305 and platform 300 combination without disassembling cords and moving surgical tools.

In some examples, channel component 300 may include a three-component system. Channel component 300 may be sterilized and, in some cases, disposable. Channel component 300 may stabilize and organize power cords, suction tubing, and other surgical tools. Channel component 300 may attaching to platform 300 after draping and prior to placement or organization of sterilized surgical tools 330, surgical accessories, etc. Accordingly, channel component 300 may efficiently organize various medical equipment (e.g., including cords 325 and tools 330, among other examples) which may reduce surgical time, decrease contamination risks, decrease reusable cord damage or accidental discarding, decrease the risk of tools 330 falling off of the sterile field or out of the sterilized region, etc.

Platform 300 is an example of, or includes aspects of, the corresponding element described with reference to FIGS. 1, 2, 4-6, and 9. Channel component 305 is an example of, or includes aspects of, the corresponding element described with reference to FIGS. 1, 2, 8, and 9. In one embodiment, channel component 305 includes channels 310 and channel locks 315. Channels 310 are examples of, or include aspects of, the corresponding element(s) described with reference to FIGS. 1, 2, 8, and 9. Channel locks 315 are examples of, or include aspects of, the corresponding element(s) described with reference to FIGS. 2 and 10.

Medical drapery 320 is an example of, or includes aspects of, the corresponding element described with reference to FIGS. 1, 2, 6, and 7. Cords 325 are examples of, or include aspects of, the corresponding element(s) described with reference to FIGS. 1, 2, and 7. Tools 330 are examples of, or include aspects of, the corresponding element(s) described with reference to FIG. 1. Patient area 335 is an example of, or includes aspects of, the corresponding element described with reference to FIGS. 1, 2, 6, and 7.

Figure 4:
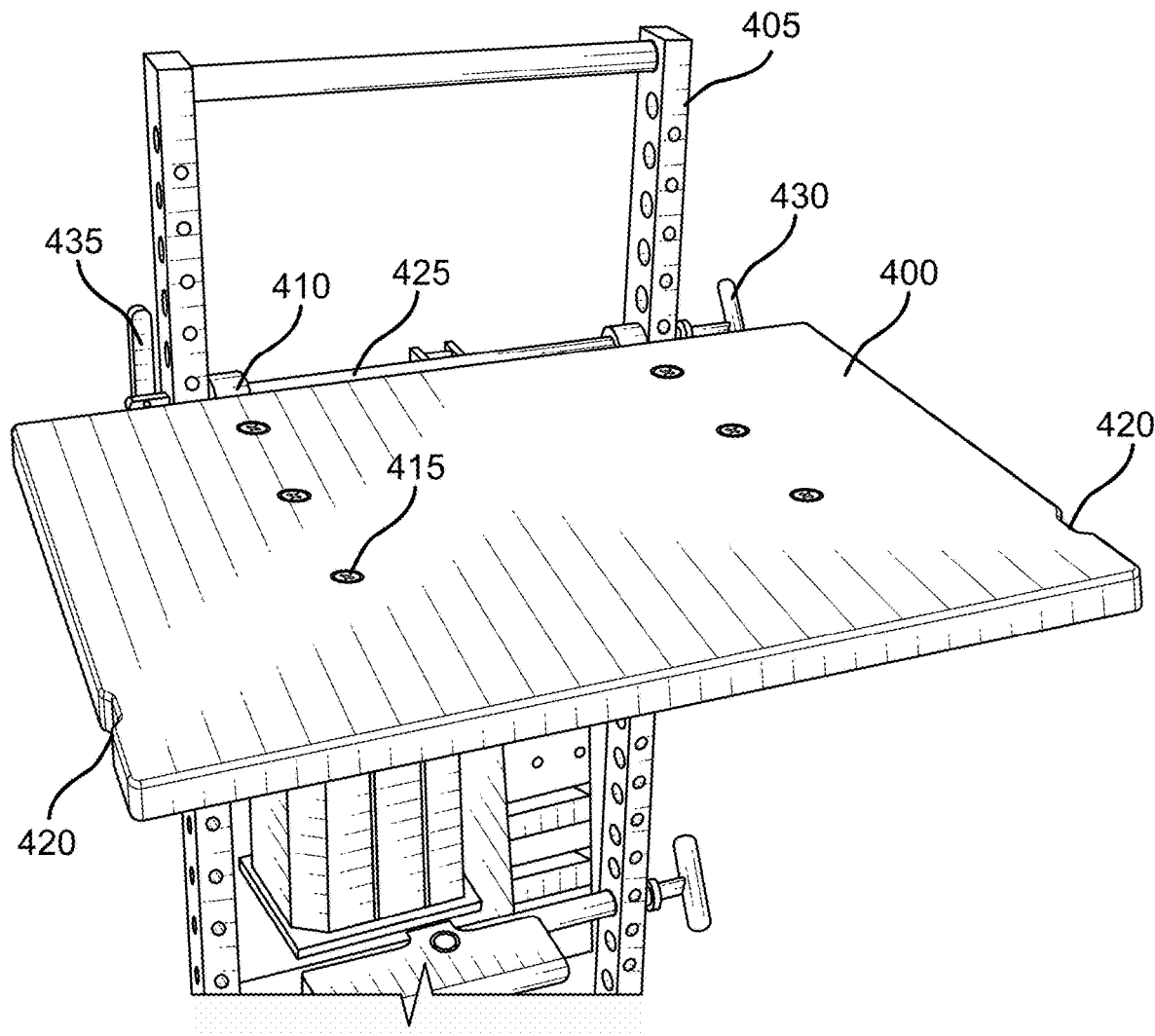
FIG. 4 shows an example of platform system according to aspects of the present disclosure.

FIG. 4 shows an example of platform 400 system according to aspects of the present disclosure. The example shown includes platform 400, frame 405, support arms 410, attachment holes 415, notches 420, support rods 425, rod handle 430, and rod lock 435. In some examples, FIG. 4 may illustrate a top/front view of platform 400, frame 405, and the various other components illustrated. As described herein, a platform 400 may connect to a frame 405 via support arms 410. For instance, support arms may be attached or fixed to the platform 400 via attachment holes 415. For instance, screws or other fasteners may attach platform 400 to the support arms 410 through attachment holes 415. Further, platform 400 may be connected or attached to frame 405 through one or more (e.g., two) support rods 425. One or more support rods 425 may be configured to be inserted through first holes in the frame 405 (e.g., which may be a surgical bed frame) and through second holes in the one or more support arms 410, thereby securing platform 400 to frame 405. In some examples, the support rods 425 may be inserted through holes in the frame and in the support arms 410 and the support rods 425 may be secured in place via rod locks 435. For instance, one end of a support rod 425 may include a rod handle 430 for placing or setting a support rod 425 into certain holes of the frame 405 and support arms 410, and an opposite end of the support rod 425 may include a rod lock 435 to secure the rod in place. In some examples, the one or more support arms 410 are permanently attached to the platform 400, and the platform 400 and support arms 410 may be separable from the frame 405 (e.g., the platform 400 and support arms 410 may be movable along the frame 405).

Platform 400 is an example of, or includes aspects of, the corresponding element described with reference to FIGS. 1-3, 5, 6, and 9. Frame 405 is an example of, or includes aspects of, the corresponding element described with reference to FIGS. 1, 2, 5, and 6. Support arms 410 are examples of, or include aspects of, the corresponding element(s) described with reference to FIGS. 1, 2, 5, and 6. Attachment holes 415 are examples of, or include aspects of, the corresponding element(s) described with reference to FIG. 1. Notches 420 are examples of, or include aspects of, the corresponding element(s) described with reference to FIG. 5. Support rods 425 are examples of, or include aspects of, the corresponding element(s) described with reference to FIGS. 1, 2, and 5. Rod handle 430 is an example of, or includes aspects of, the corresponding element described with reference to FIG. 5. Rod lock 435 is an example of, or includes aspects of, the corresponding element described with reference to FIG. 5.

Figure 5:
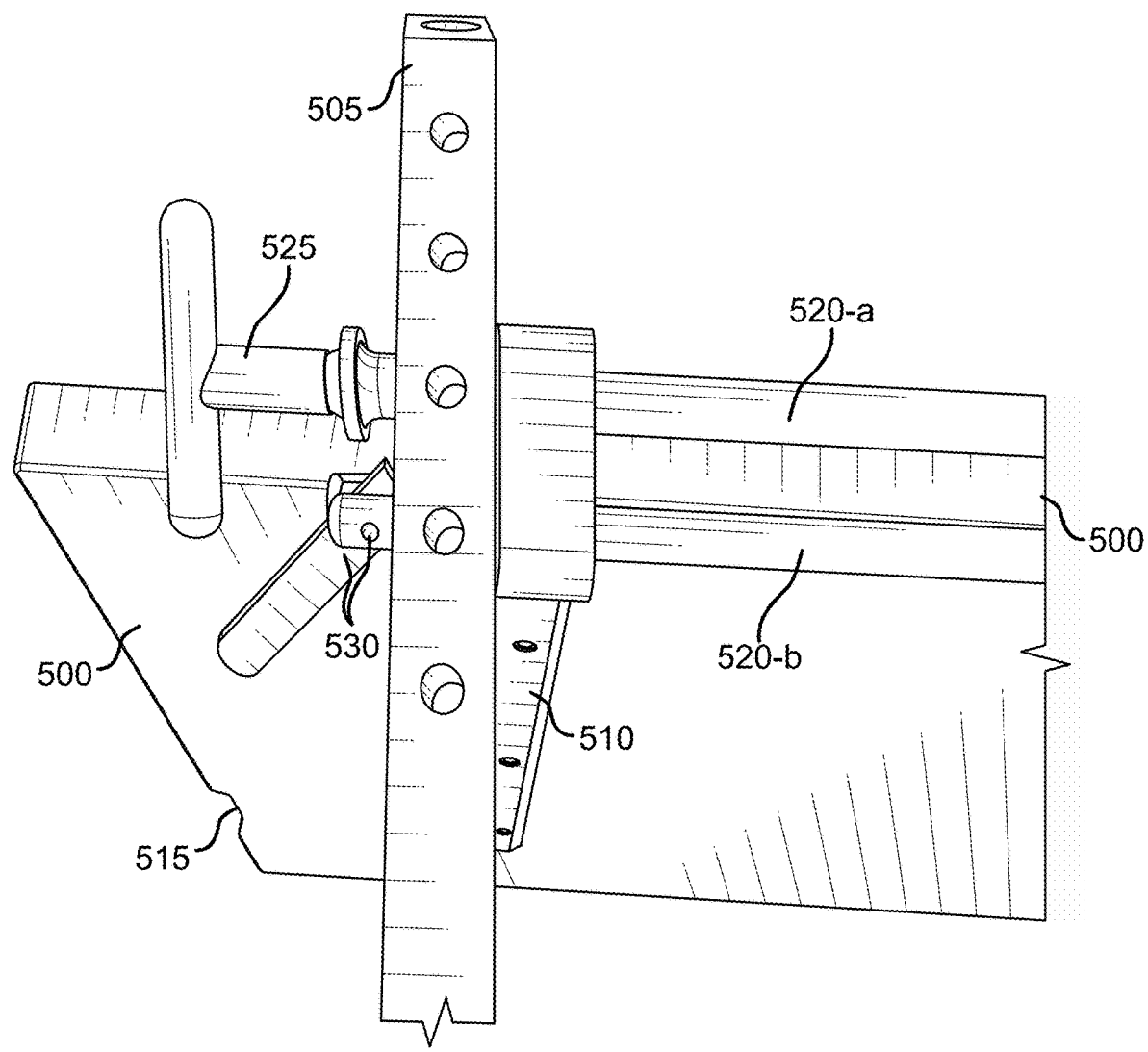
FIG. 5 shows an example of platform attachment diagram according to aspects of the present disclosure.

FIG. 5 shows an example of platform 500 attachment diagram according to aspects of the present disclosure. The example shown includes platform 500, frame 505, support arms 510, notches 515, support rods 520, rod handle 525, and rod lock 530. FIG. 5 may illustrate one or more aspects of the platform 400 and frame 405 (e.g., among other components) described with reference to FIG. 4. For instance, FIG. 5 may illustrate platform 400 and frame 405 from an opposite side (e.g., a rear/bottom view relative to the view illustrated in FIG. 4).

In some examples, platform 500 may be connected or attached to support arms 510 on the bottom of platform 500 (e.g., where a screw or other fastener may connect platform 500 to the support arms 510 through attachment holes 415 on the top of platform 500, as described with reference to FIG. 4). Platform 500 may be connected or attached to frame 505 two support rods 520 (e.g., support rod 520-*a* and support rode 520-*b*). Support rod 520-*a* and support rode 520-*b* may be configured to be inserted through first holes in the frame 505 (e.g., which may be a surgical bed frame) and through second holes in the one or more support arms 510, thereby securing platform 500 to frame 505. In some examples, Support rod 520-*a* and support rode 520-*b* may be inserted through holes in the frame 505 and in the support arms 510, and support rod 520-*a* and support rode 520-*b* may be secured in place via rod locks 530. For instance, one end of a support rod 520 may include a rod handle 525 for placing or setting a support rod 525 into certain holes of the frame 505 and support arms 510, and an opposite end of the support rod 520 may include a rod lock 530 to secure the rod in place. In the example of FIG. 5, support rod 520-*a* and support rode 520-*b* may be inserted at opposite ends of the frame 505 such that a rod handle 525 of support rod 520-*a* is at an opposite end as a rod handle 525 of support rode 520-*b*. In some examples, the one or more support arms 510 are permanently attached to the platform 500, and the platform 500 and support arms 510 may be separable from the frame 505 (e.g., the platform 500 and support arms 510 may be movable along the frame 505 via adjustment of support rod 520-*a* and support rode 520-*b*).

Figure 9:
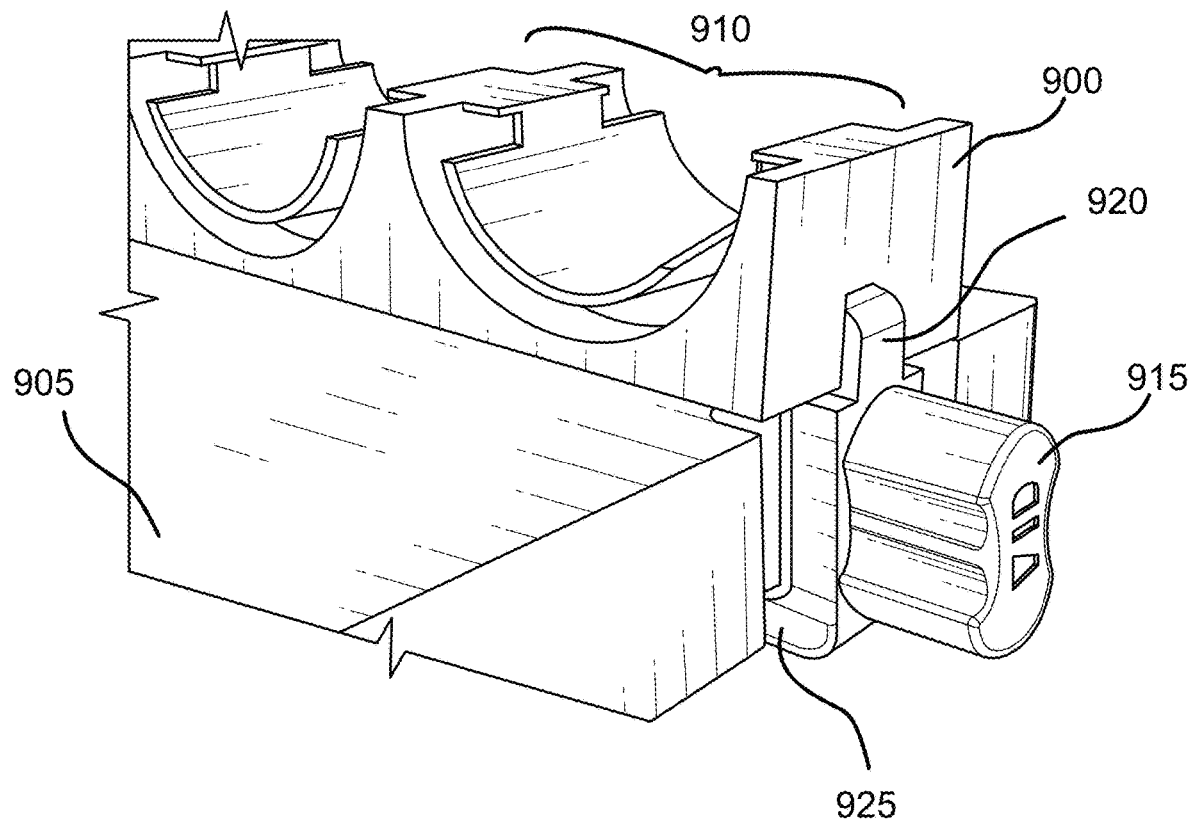
FIG. 9 shows an example of channel component attachment diagram according to aspects of the present disclosure.

Platform 500 may be attached to the support arms 505. The support arms 505 may be attached to platform scaffolding 515, where the support arms 505 and the platform scaffolding 515 may be adjustable, providing the platform 500 with multiple height options. The notches 515 may be used to align (e.g., and attach) the channel component to the platform 500 (e.g., as shown in FIG. 9). Platform 500 is an example of, or includes aspects of, the corresponding element described with reference to FIGS. 1-4, 6, and 9. Frame 505 is an example of, or includes aspects of, the corresponding element described with reference to FIGS. 1, 2, 4, and 6. Support arms 510 may be examples of, or include aspects of, the corresponding element(s) described with reference to FIGS. 1, 2, and 4. Notches 515 may be examples of, or include aspects of, the corresponding element(s) described with reference to FIG. 4. Support rods 520 may be examples of, or include aspects of, the corresponding element(s) described with reference to FIGS. 1, 2, and 4. Rod handle 525 is an example of, or includes aspects of, the corresponding element described with reference to FIG. 4. Rod lock 530 is an example of, or includes aspects of, the corresponding element described with reference to FIG. 4.

Figure 6:
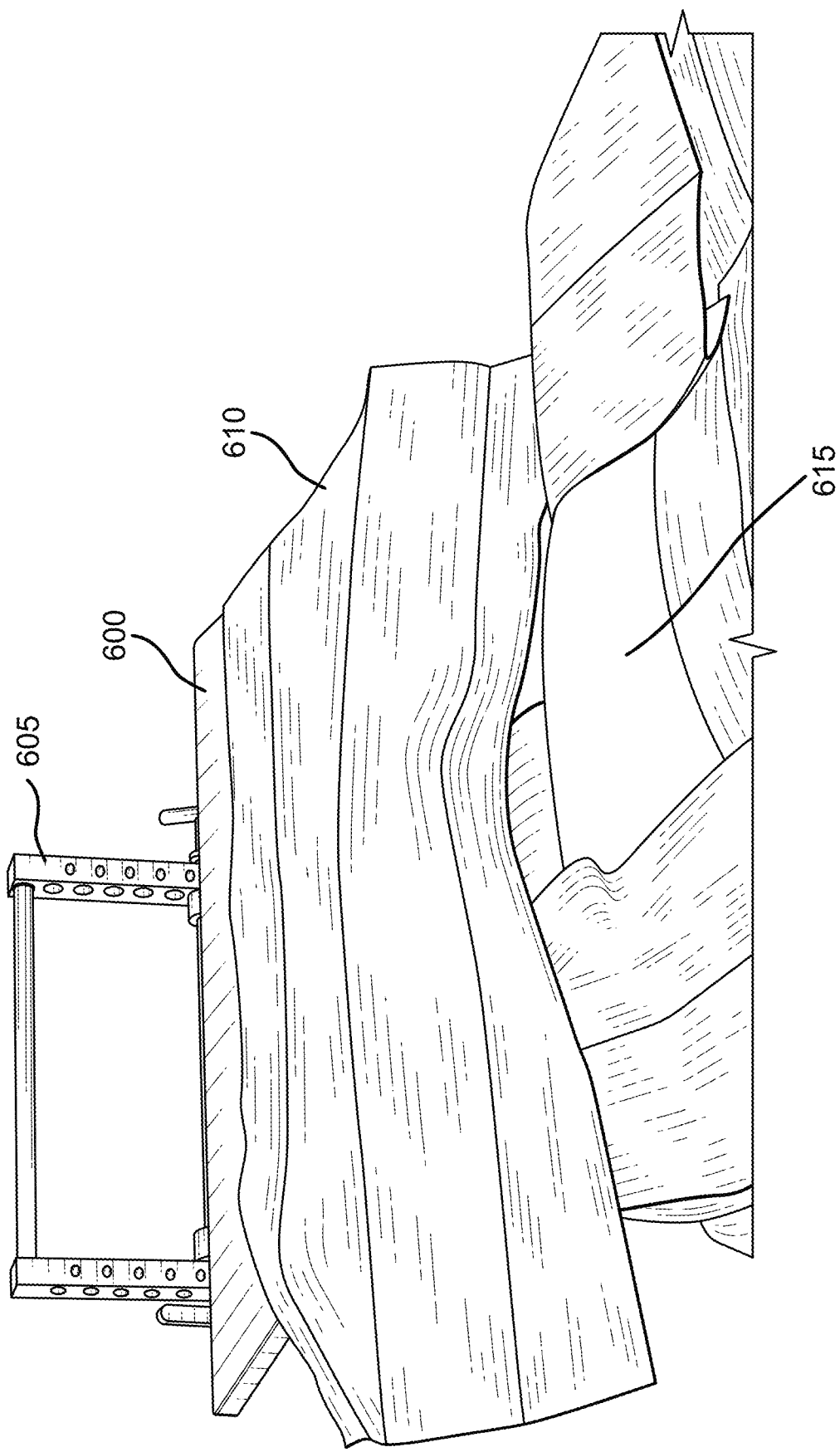
FIGS. 6 and 7 show examples of system for securing medical components according to aspects of the present disclosure.

FIG. 6 shows an example of system for securing medical components according to aspects of the present disclosure. The example shown includes platform 600, frame 605, medical drapery 610, and patient area 615. Medical drapery 610 may be placed on platform 600 and extend to and/or around patient area 615. As described, the platform component (platform 600) may attach to a bed frame (frame 605) above a patient after the patient is in place for a medical procedure. Medical drapery 610 may be placed on or around the platform 600 for sterilization purposes. For instance, sterile medical drapery 610 may be placed over platform 600, and in some cases over frame 605, and the sterile medical drapery 610 may be formed around a patient area 615 to establish a sterile field or a sterilized region. As described herein, a channel component may then be attached to, or placed on, the platform 600 to secure the medical drapery 610 (e.g., medical drapery 610 may be placed between the platform 600 and the channel component to hold the medical drapery 610 in place for reduced pathogen or infection risk). Accordingly, sterile medical drapery 610 may cover platform 600 and a sterile channel component may be attached to the platform to secure the sterile medical drapery 610 and secure/organize additional sterile equipment to establish a sterile surgical setup.

Platform 600 is an example of, or includes aspects of, the corresponding element described with reference to FIGS. 1-5, and 9. Frame 605 is an example of, or includes aspects of, the corresponding element described with reference to FIGS. 1, 2, 4, and 5. Medical drapery 610 is an example of, or includes aspects of, the corresponding element described with reference to FIGS. 1-3, and 7. Patient area 615 is an example of, or includes aspects of, the corresponding element described with reference to FIGS. 1-3, and 7.

Figure 7:
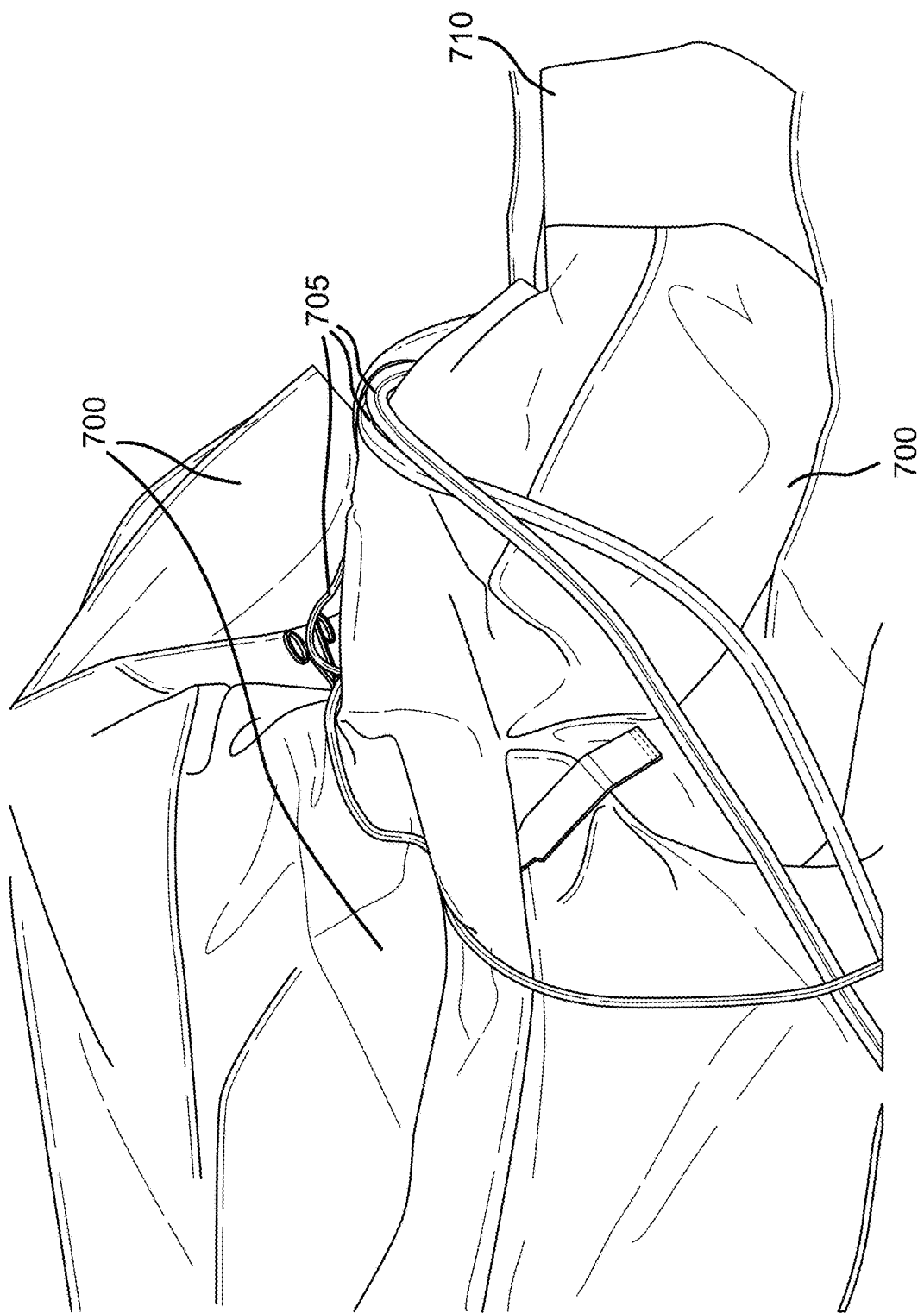

FIG. 7 shows an example of system for securing medical components according to aspects of the present disclosure. The example shown includes medical drapery 700, cords 705, and patient area 710. FIG. 7 shows an example scenario of a disorganized surgical table without the use of the channel component apparatus and techniques for implementing the channel component apparatus described herein. Medical drapery 700 and cords 705 are shown as poorly organized. Medical devices may not be readily discernible from other devices, leading to possible mistakes or timeliness during a surgical procedure. In some cases, without the techniques and apparatuses described herein, medical drapery 700 may become dislodged, tangled, inconvenient, etc. (e.g., which may compromise patient area 710). Further, disorganized medical equipment (e.g., such as various cords 705) which may compromise patient area 710 (e.g., compromise a sterile field or region surrounding patient area 710), increase surgical time, increase contamination risks, increase reusable cord 705 damage or accidental discarding, increase the risk of tools or cords 705 falling off of the sterile field or out of the sterilized region, etc. As described herein, a platform and channel component may be implemented to secure medical drapery 700, as well as to organize and secure cords 705.

Medical drapery 700 is an example of, or includes aspects of, the corresponding element described with reference to FIGS. 1-3, and 6. Cords 705 are examples of, or include aspects of, the corresponding element(s) described with reference to FIGS. 1-3. Patient area 710 is an example of, or includes aspects of, the corresponding element described with reference to FIGS. 1-3, and 6.

Figure 8:
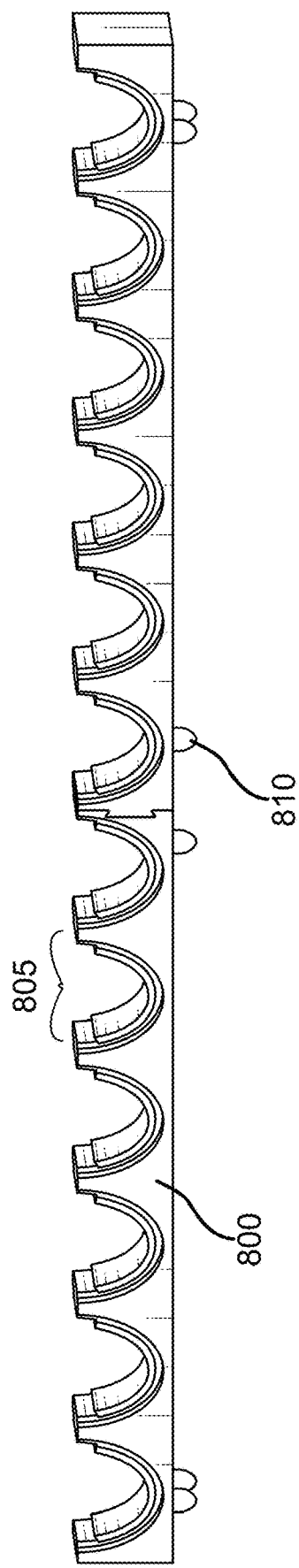
FIG. 8 shows an example of channel component diagram according to aspects of the present disclosure.

FIG. 8 shows an example of channel component 800 diagram according to aspects of the present disclosure. As described herein, channel component 800 may include a plurality of channels 805. Channels 805 may be coupled with channel locks (e.g., as illustrated in more detail herein, for example, with reference to FIG. 10) to secure and organize cords, tubes, tools, medical equipment, etc. In some cases, channel component 800 may include pegs 810 (e.g., which, in some examples, may be used to attach channel component 800 to a platform). Channel component 800 is an example of, or includes aspects of, the corresponding element described with reference to FIGS. 1-3, and 9. In one embodiment, channel component 800 includes channels 805 and pegs 810. Channels 805 is an example of, or includes aspects of, the corresponding element described with reference to FIGS. 1-3, and 9.

FIG. 9 shows an example of channel component 900 attachment diagram according to aspects of the present disclosure. The example shown includes channel component 900, platform 905, channels 910, attachment piece 915, top extension 920, and bottom extension 925. As described herein, attachment piece 915 may include a top extension 920 and a bottom extension 925. The attachment piece 915 may be configured to secure an end of the channel component 900 to a side of the platform 905 (e.g., where each side of the platform 905 may include a groove configured to receive the attachment piece 915, and where the channel component 900 comprises an attachment notch configured to receive the top extension 920). In some cases, the bottom extension 925 comprises an extension peg, and the platform 905 comprises an extension peg hole configured to receive the bottom extension peg 925.

Channel component 900 is an example of, or includes aspects of, the corresponding element described with reference to FIGS. 1-3, and 8. Platform 905 is an example of, or includes aspects of, the corresponding element described with reference to FIGS. 1-6. Channels 910 are examples of, or include aspects of, the corresponding element(s) described with reference to FIGS. 1-3, and 8. Attachment piece 915 is an example of, or includes aspects of, the corresponding element(s) described with reference to FIGS. 1 and 2.

FIG. 9 illustrates one example of how a channel component 900 may be attached to a platform 905 (e.g., securing medical drapery therebetween). However, such is shown for illustrative purposes and is not intended to be limiting in terms of scope of the present disclosure. For instance, various other attachment mechanisms may be implemented by analogy, without departing from the scope of the present disclosure. As described herein, channel 900 may additionally or alternatively include pegs (e.g., pegs 810) that may be inserted into peg holes of a platform 905. Additionally or alternatively, attachment piece 915 may include a clamp, a hinged clamp, a vice, a bracket, an adhesive, or various other attachment mechanisms.

Figure 10:
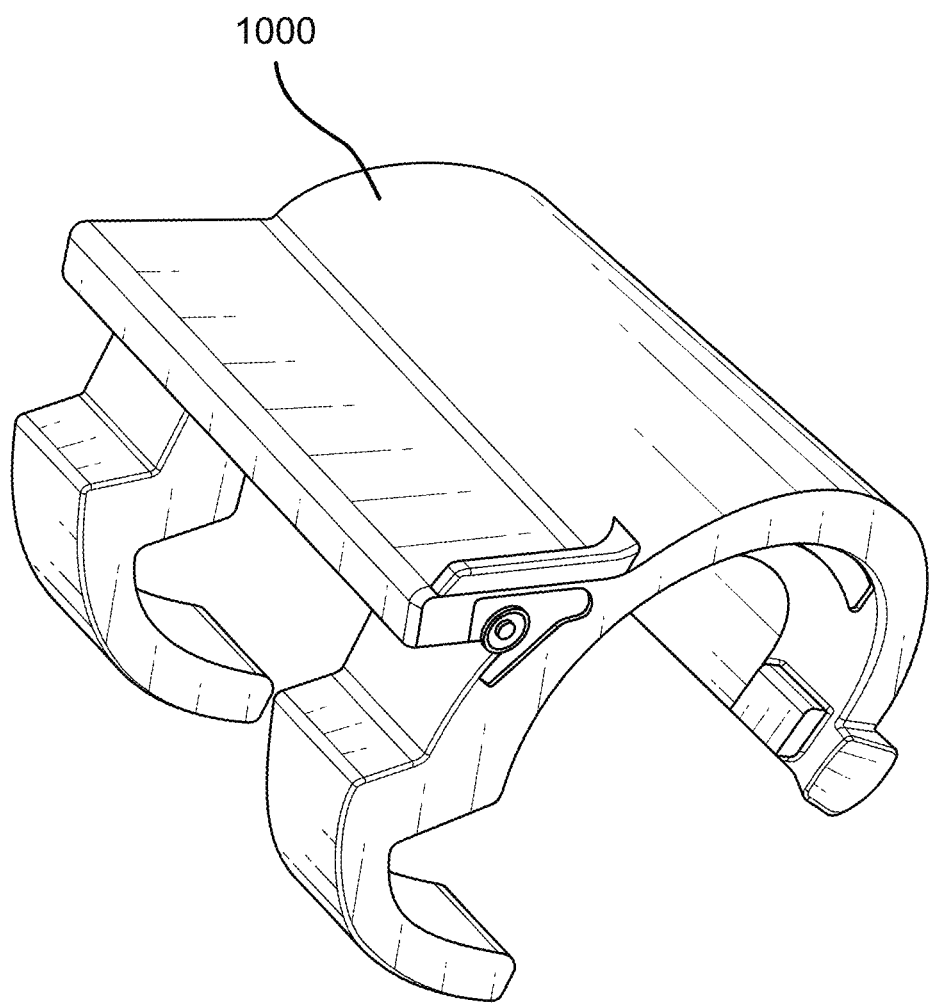
FIG. 10 shows an example of channel lock diagram according to aspects of the present disclosure.

FIG. 10 shows an example of channel lock 1000 diagram according to aspects of the present disclosure. Channel lock 1000 may attach to a channel component (e.g., channel of a channel component, which may comprise a portion of a cylinder with an opening configured to receive a cord). In some examples, channel lock 1000 may turn around a longitudinal axis to provide and OPEN and CLOSED position. In the OPEN position, cords may be placed in and removed from the channel. In the CLOSED position, the cords may be secured in place while providing the cords the ability to move in a longitudinal direction, as needed by a surgical team (e.g., without pinching or damaging the cords). Channel lock 1000 is shown for illustrative purposes and is not intended to be limiting in terms of scope of the present disclosure. For instance, various other lock mechanisms may be implemented by analogy, without departing from the scope of the present disclosure. Channel lock 1000 is an example of, or includes aspects of, the corresponding element(s) described with reference to FIGS. 2 and 3.

Figure 11:
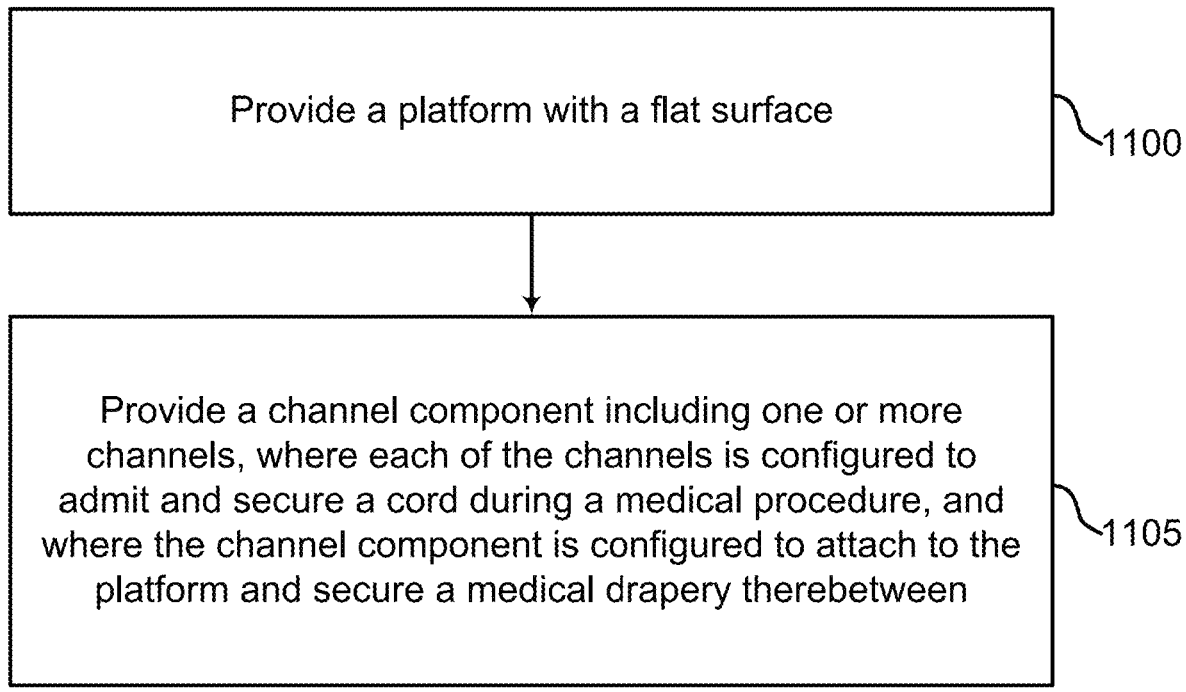
FIG. 11 shows an example of a process for securing medical components according to aspects of the present disclosure.

FIG. 11 shows an example of a process for securing medical components according to aspects of the present disclosure. In some examples, these operations are performed by a system including a processor executing a set of codes to control functional elements of an apparatus. Additionally or alternatively, certain processes are performed using special-purpose hardware. Generally, these operations are performed according to the methods and processes described in accordance with aspects of the present disclosure. In some cases, the operations described herein are composed of various substeps, or are performed in conjunction with other operations.

At operation 1100, the system provides a platform with a flat surface. In some cases, the operations of this step refer to, or be performed by, a platform as described with reference to FIGS. 1-6, and 9.

At operation 1105, the system provides a channel component including one or more channels, where each of the channels is configured to admit and secure a cord during a medical procedure, and where the channel component is configured to attach to the platform and secure a medical drapery therebetween. In some cases, the operations of this step refer to, or be performed by, a channel component as described with reference to FIGS. 1-3, 8, and 9.

Figure 12:
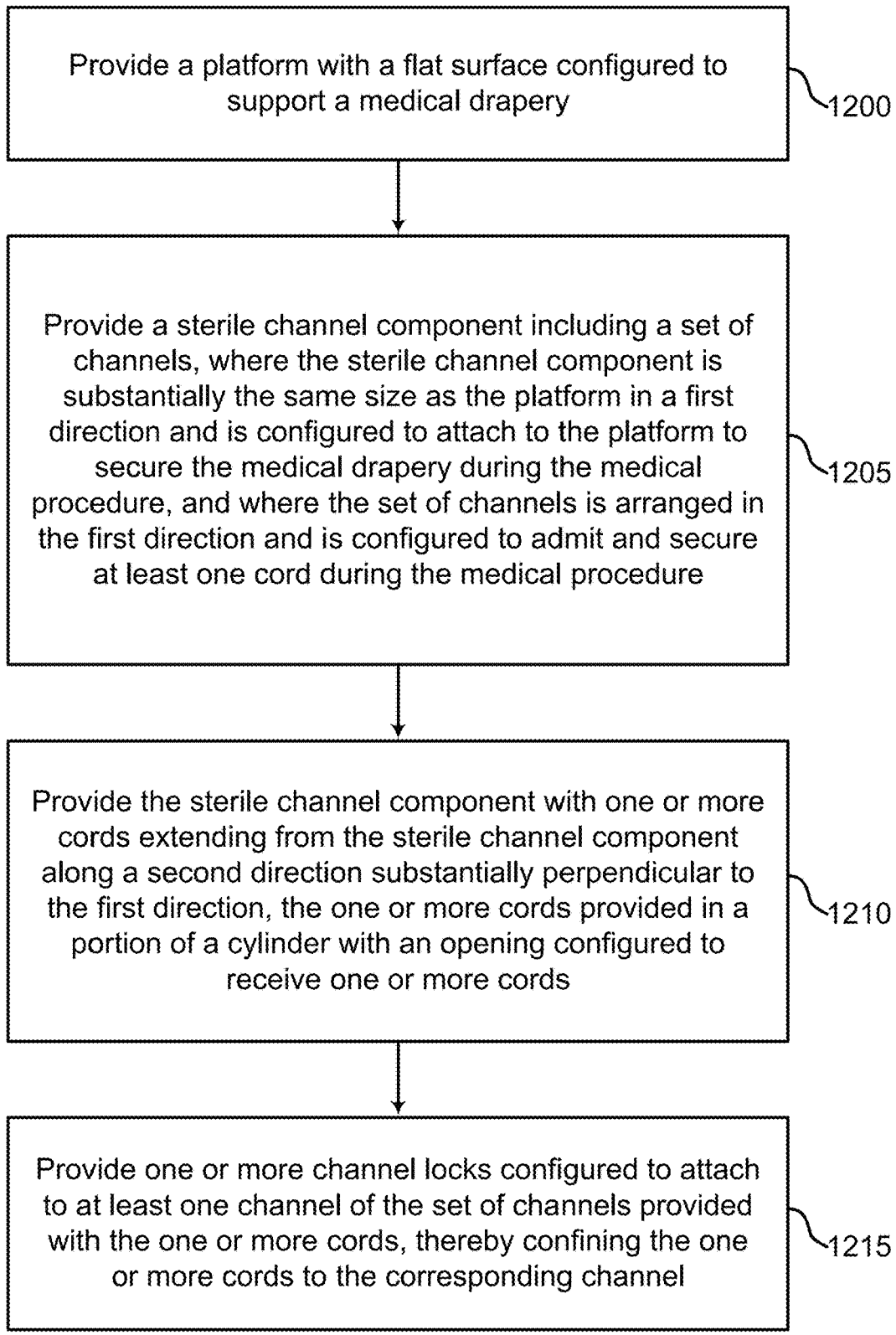
FIG. 12 shows an example of a process for performing a medical procedure according to aspects of the present disclosure.

FIG. 12 shows an example of a process for performing a medical procedure according to aspects of the present disclosure. In some examples, these operations are performed by a system including a processor executing a set of codes to control functional elements of an apparatus. Additionally or alternatively, certain processes are performed using special-purpose hardware. Generally, these operations are performed according to the methods and processes described in accordance with aspects of the present disclosure. In some cases, the operations described herein are composed of various substeps, or are performed in conjunction with other operations.

At operation 1200, the system provides a platform with a flat surface configured to support a medical drapery. In some cases, the operations of this step refer to, or be performed by, a platform as described with reference to FIGS. 1-6, and 9.

At operation 1205, the system provides a sterile channel component including a set of channels, where the sterile channel component is substantially the same size as the platform in a first direction and is configured to attach to the platform to secure the medical drapery during the medical procedure, and where the set of channels is arranged in the first direction and is configured to admit and secure at least one cord during the medical procedure. In some cases, the operations of this step refer to, or be performed by, a channel component as described with reference to FIGS. 1-3, 8, and 9.

At operation 1210, the system provides the sterile channel component with one or more cords extending from the sterile channel component along a second direction substantially perpendicular to the first direction, the one or more cords provided in a portion of a cylinder with an opening configured to receive one or more cords. In some cases, the operations of this step refer to, or be performed by, a channels as described with reference to FIGS. 1-3, 8, and 9.

At operation 1215, the system provides one or more channel locks configured to attach to at least one channel of the set of channels provided with the one or more cords, thereby confining the one or more cords to the corresponding channel. In some cases, the operations of this step refer to, or be performed by, a channel locks as described with reference to FIGS. 2 and 3.

Accordingly, the present disclosure includes the following embodiments.

An apparatus for securing medical components is described. Embodiments of the apparatus include a platform with a flat surface and a channel component comprising one or more channels, wherein each of the channels is configured to admit and secure a cord during a medical procedure, and wherein the channel component is configured to attach to the platform and secure a medical drapery therebetween.

A method of manufacturing an apparatus for securing medical components is described. The method includes a platform with a flat surface and a channel component comprising one or more channels, wherein each of the channels is configured to admit and secure a cord during a medical procedure, and wherein the channel component is configured to attach to the platform and secure a medical drapery therebetween.

In some examples, the platform comprises one or more holes, and the channel component comprises one or more pegs corresponding to the one or more holes, wherein the holes are configured to receive the pegs with the medical drapery therebetween.

Some examples of the apparatus, system, and method described above further include one or more attachment pieces including a top extension and a bottom extension and configured to secure one or more ends of the channel component to one or more sides of the platform, wherein each of the one or more sides of the platform comprises a groove configured to receive the one or more attachment pieces, and wherein the channel component comprises an attachment notch configured to receive the top extension.

In some examples, the bottom extension comprises an extension peg, and the platform comprises an extension peg hole configured to receive the extension peg. In some examples, each of the channels comprises a portion of a cylinder with an opening configured to receive the cord.

Some examples of the apparatus, system, and method described above further include one or more channel locks configured to attach to one of the channels, thereby confining the cord to the corresponding channel.

In some examples, each of the channel locks comprises a sliding portion, and each of the channels comprises a groove configured to receive the sliding portion, and wherein each of the channel locks further comprises a notch configured to secure the channel lock in a closed position.

Some examples of the apparatus, system, and method described above further include one or more support arms configured to attach to the platform and to a surgical bed frame. Some examples of the apparatus, system, and method described above further include one or more support rods configured to be inserted through first holes in the surgical bed frame and through second holes in the one or more support arms, thereby securing the apparatus to the surgical bed frame.

In some examples, the one or more support arms may be permanently attached to the platform, and the channel component is separable from the platform. In some examples, the cord comprises an electrical cord, a bipolar cord, a suction tube, a water tube, a drill cord, a smoke evacuation cord, an electrocautery cord, an electrical stimulation cord, or any combination thereof.

An apparatus for securing medical components is described. Embodiments of the apparatus include a platform with a flat surface configured to support a medical drapery and a channel component comprising a plurality of channels. The channel component may be substantially the same size as the platform in a first direction and may be configured to attach to the platform to secure the medical drapery during a medical procedure. The plurality of channels may be arranged in the first direction and may be configured to admit and secure at least one cord during the medical procedure.

A method of manufacturing an apparatus for securing medical components is described. The method includes a platform with a flat surface configured to support a medical drapery and a channel component comprising a plurality of channels, wherein the channel component is substantially the same size as the platform in a first direction and may be configured to attach to the platform to secure the medical drapery during a medical procedure, and wherein the plurality of channels is arranged in the first direction and is configured to admit and secure at least one cord during the medical procedure.

In some examples, each of the channels in the plurality of channels comprises a portion of a cylinder with an opening configured to receive one or more cords, the one or more cords extending from the channel component along a second direction substantially perpendicular to the first direction. In some examples, the platform is configured to be movable in a third direction while the attached channel component secures the at least one cord during the medical procedure, the third direction being substantially perpendicular to a plane formed by the first direction and the second direction.

Some examples of the apparatus, system, and method described above further include one or more channel locks configured to attach to at least one channel of the plurality of channels, thereby confining one or more cords to the corresponding channel.

In some examples, the channel component and the one or more channel locks are sterilizable. In some examples, the platform is configured to support one or more surgical tools in addition to the attached channel component.

The description and drawings described herein represent example configurations and do not represent all the implementations within the scope of the claims. For example, the operations and steps may be rearranged, combined or otherwise modified. Also, structures and devices may be represented in the form of block diagrams to represent the relationship between components and avoid obscuring the described concepts. Similar components or features may have the same name but may have different reference numbers corresponding to different figures.

Some modifications to the disclosure may be readily apparent to those skilled in the art, and the principles defined herein may be applied to other variations without departing from the scope of the disclosure. Thus, the disclosure is not limited to the examples and designs described herein, but is to be accorded the broadest scope consistent with the principles and novel features disclosed herein.

In this disclosure and the following claims, the word "or" indicates an inclusive list such that, for example, the list of X, Y, or Z means X or Y or Z or XY or XZ or YZ or XYZ. Also the phrase "based on" is not used to represent a closed set of conditions. For example, a step that is described as "based on condition A" may be based on both condition A and condition B. In other words, the phrase "based on" shall be construed to mean "based at least in part on." Also, the words "a" or "an" indicate "at least one."

What is claimed is:

1. An apparatus for securing medical components, comprising:

a platform with a flat surface;

a channel component comprising one or more channels, wherein each of the one or more channels is configured to admit and secure a cord during a medical procedure, and wherein the channel component is configured to attach to the platform and secure a medical drapery therebetween; and one or more attachment pieces including a top extension and a bottom extension and configured to secure one or more ends of the channel component to one or more sides of the platform, respectively, wherein each of the one or more sides of the platform comprises a groove configured to receive the one or more attachment pieces, and wherein the channel component is connected to the top extension.

2. The apparatus of claim 1, wherein:
the platform comprises one or more holes, and the channel component comprises one or more pegs corresponding to the one or more holes, wherein the holes are configured to receive the pegs with the medical drapery therebetween.

3. The apparatus of claim 1, wherein:
the bottom extension comprises an extension peg, and the platform comprises an extension peg hole configured to receive the extension peg.

4. The apparatus of claim 1, wherein:
each of the channels comprises a portion of a cylinder with an opening configured to receive the cord.

5. The apparatus of claim 1, further comprising:
one or more channel locks configured to attach to one of the one or more channels, thereby confining the cord to the corresponding channel.

6. The apparatus of claim 5, wherein:
each of the one or more channel locks comprises a sliding portion, and each of the one or more channels comprises a groove configured to receive the sliding portion, and wherein each of the one or more channel locks is connected to the one or more channels in a closed position.

7. The Apparatus of claim 1, further comprising:
one or more support arms configured to attach to the platform and to a surgical bed frame.

8. The apparatus of claim 7, further comprising:
one or more support rods configured to be inserted through first holes in the surgical bed frame and through second holes in the one or more support arms, thereby securing the apparatus to the surgical bed frame.

9. The apparatus of claim 7, wherein:
the one or more support arms are permanently attached to the platform, and the channel component is separable from the platform.

10. The apparatus of claim 1, wherein:
the cord comprises an electrical cord, a bipolar cord, a suction tube, a water tube, a drill cord, a smoke evacuation cord, an electrocautery cord, an electrical stimulation cord, or any combination thereof.

11. A method of manufacturing an apparatus for securing medical components, the method comprising:
providing a platform with a flat surface;
providing a channel component comprising one or more channels, wherein each of the channels is configured to admit and secure a cord during a medical procedure, and wherein the channel component is configured to attach to the platform and secure a medical drapery therebetween; and providing one or more attachment pieces including a top extension and a bottom extension and configured to secure one or more ends of the channel component to one or more sides of the platform, respectively, wherein each of the one or more sides of the platform comprises a groove configured to receive the one or more attachment pieces, and wherein the channel component is connected to the top extension.

12. The method of claim 11, wherein:

the platform comprises one or more holes, and the channel component comprises one or more pegs corresponding to the one or more holes, wherein the holes are configured to receive the pegs with the medical drapery therebetween.

13. An apparatus for performing a medical procedure, comprising:
- a platform with a flat surface configured to support a medical drapery;
- a channel component comprising a plurality of channels, wherein the channel component is substantially the same size as the platform in a first direction and is configured to attach to the platform to secure the medical drapery during the medical procedure, and wherein the plurality of channels is arranged in the first direction and is configured to admit and secure at least one cord during the medical procedure;
- one or more support arms configured to attach to the platform and to a surgical bed frame; and
- one or more support rods configured to be inserted through first holes in the surgical bed frame and through second holes in the one or more support arms, thereby securing the apparatus to the surgical bed frame.

14. The apparatus of claim 13, wherein:

each of the channels in the plurality of channels comprises a portion of a cylinder with an opening configured to receive one or more cords, the one or more cords extending from the channel component along a second direction substantially perpendicular to the first direction.

15. The apparatus of claim 14, wherein:

the platform is configured to be movable in a third direction while the attached channel component secures the at least one cord during the medical procedure, the third direction being substantially perpendicular to a plane formed by the first direction and the second direction.

16. The apparatus of claim 13, further comprising:

one or more channel locks configured to attach to at least one channel of the plurality of channels, thereby confining one or more cords to the corresponding channel.

17. The apparatus of claim 13, wherein:

the platform is configured to support one or more surgical tools in addition to the attached channel component.

* * * * *